United States Patent
D'Sa et al.

(10) Patent No.: US 6,322,532 B1
(45) Date of Patent: Nov. 27, 2001

(54) SONOPHORESIS METHOD AND APPARATUS

(75) Inventors: Joseph M. D'Sa, Woodbury; Jaimeson C. Keister, Lakeville, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/329,577

(22) Filed: Jun. 10, 1999

Related U.S. Application Data (60) Provisional application No. 60/090,562, filed on Jun. 24, 1998.

(51) Int. Cl.[7] .................................................. A61B 17/20
(52) U.S. Cl. ............................ 604/22; 604/289; 604/290
(58) Field of Search .................................. 604/20–22, 19, 604/289, 290

(56) References Cited

U.S. PATENT DOCUMENTS

| | | |
|---|---|---|
| 4,191,904 * | 3/1980 | Massa .................................... 310/322 |
| 4,272,051 | 6/1981 | Huggins . |
| 4,305,403 | 12/1981 | Dunn . |
| 4,660,802 | 4/1987 | Oscarsson . |
| 4,697,785 | 10/1987 | Tuseth . |
| 4,702,740 | 10/1987 | Bates . |
| 4,767,402 | 8/1988 | Kost et al. . |
| 4,780,212 | 10/1988 | Kost et al. . |
| 4,929,860 | 5/1990 | Hulsing, II et al. . |
| 4,948,587 | 8/1990 | Kost et al. . |
| 5,084,035 | 1/1992 | Salvadori et al. . |
| 5,256,920 * | 10/1993 | Porzio ...................................... 310/13 |
| 5,452,267 | 9/1995 | Spevak . |
| 5,618,275 | 4/1997 | Bock . |
| 5,656,016 | 8/1997 | Ogden . |
| 5,722,397 | 3/1998 | Eppstein . |
| 5,814,599 * | 9/1998 | Mitragotri et al. ..................... 604/20 |

FOREIGN PATENT DOCUMENTS

| | | |
|---|---|---|
| 2945243-A1 * | 5/1980 | (DE) . |
| 19624204-C1 * | 10/1997 | (DE) . |
| 0524371B1 | 9/1994 | (EP) . |
| 0678853-A2 * | 10/1995 | (EP) . |
| 1089788-A1 * | 12/1999 | (EP) . |
| 94/08655 | 4/1994 | (WO) . |
| 97/04832 | 2/1997 | (WO) . |
| 98/17184 | 4/1998 | (WO) . |
| WO-99/66980-A1 * | 12/1999 | (WO) . |

* cited by examiner

*Primary Examiner*—Richard K. Seidel
*Assistant Examiner*—Jeremy Thissell
(74) *Attorney, Agent, or Firm*—Ted K. Ringsred; MarySusan Howard; Robert W. Sprague (57) ABSTRACT

An ultrasonic transducer that operates in flexure mode provides a highly efficient and compact sonophoresis device. Such a device is particularly useful for efficiently enhancing permeation of a substance through a membrane, such as dermal and mucosal membranes for purposes of transdermal/transmucosal drug delivery and/or body fluid monitoring.

44 Claims, 2 Drawing Sheets

SONOPHORESIS METHOD AND APPARATUS

This application claims benefit of Provisional No. 60/090,562 filed Jun. 24, 1998.

FIELD

The present invention relates to an improved sonophoresis method and apparatus for enhancing transport of a substance through a liquid and, in particular, enhancing permeation of a substance into and/or across a membrane, such as for transdermal/transmucosal drug delivery and non-invasive monitoring of body fluids.

BACKGROUND

The term "sonophoresis" refers to the use of acoustic, usually ultrasonic, wave energy to enhance the transport of a substance through a liquid medium. The acoustic compression waves induce "streaming" and/or "cavitation" in the liquid medium. Streaming is a phenomenon that occurs when an oscillation in a liquid or gaseous medium forces the medium molecules to convect away from the source, which results in a net flow of agent or drug away from the wave source. Cavitation refers to the formation of bubbles in a liquid subjected to intense vibrations. It is often associated, for example, with the action of a propeller blade moving through water. In that context, cavitation is considered undesirable because it can cause erosive pitting of the propeller blade. However, cavitation may also be intentionally generated using high intensity acoustic waves, and there is a wide range of circumstances where it may be desired to do so. For example, cavitation can be useful in the context of such things as ultrasonic cleaning, and electroplating and electrochemistry processes.

One particularly important area where sonophoresis has been used is in the context of transdermal and transmucosal drug delivery. Conventional passive transdermal/transmucosal drug delivery systems are often ineffective at delivering large molecules into and/or across the dermal and mucosal membranes. It has been found, however, that transmembranal sonophoresis (i.e., the use of sonophoresis to enhance diffusion of a substance across a membrane) can be effectively used for transdermal/transmucosal drug delivery. U.S. Pat. Nos. 4,780,212, 4,767,402, and 4,948,587 to Kost, et al., U.S. Pat. No. 5,618,275 to Bock, U.S. Pat. No. 5,656,016 to Ogden, and U.S. Pat. No. 5,722,397 to Eppstein (all hereby incorporated by reference) disclose various sonophoresis systems.

In these conventional systems, sonophoresis is produced with a transducer made of a piezoelectric material that vibrates by simply expanding and contracting axially in response to an applied electrical voltage signal. When used for transdermal/transmucosal drug delivery, the waves generated by the sonophoresis transducer are applied to a drug-containing medium on the skin or mucosal tissue. By selecting piezoelectric material having an appropriate size and shape and applying a suitable voltage signal frequency, the resulting acoustic waves enhance permeation of the drug through the dermal/mucosal membrane.

The precise mechanism by which the acoustic waves help to enhance permeability through the skin/mucosal tissue is not fully understood. Without wishing to be bound by any theory, it is hypothesized that the acoustic waves cause microcavitation in the drug medium and the skin itself, and this action helps the drug molecules to diffuse into and through the skin. It is further hypothesized that the ordered lipid layers in parts of the skin may be temporarily disrupted by the acoustic waves, thus permitting molecules to pass. In any event, regardless of the mechanism(s) at work, the result is that the acoustic waves enhance passage of substances into and/or through the membrane.

There are two basic types of conventional sonophoresis transducer used. The first type is constructed of a converter and a horn section. The converter is made up of a stack of piezoelectric disks designed to vibrate in an axial direction. This so-called "horn type" of sonophoresis device, although potentially quite efficient at producing cavitation and permeation enhancement, is typically about 20 cm long and weighs as much as a kilogram. These large and heavy devices are cumbersome and obviously would not be desirable for many applications.

The second type of conventional sonophoresis transducer device does not have large converter and horn sections. It relies instead on only one or a small number of piezoelectric disk layers which, as with the horn type device, vibrate in a simple axial mode. Although these "disk type" of sonophoresis transducers can be relatively small and lightweight, they are generally not operated at resonance and thus are very inefficient, i.e., requiring a large amount of power to achieve suitable penetration enhancement. By way of comparison, for effective penetration enhancement a typical 20 cm long horn type device may only require on the order of about 0.1 to 0.2 watts/cm$^2$ of surface area of the relevant wave-generating surface (usually against the skin or mucosa); whereas a conventional disk type device of less than 2 cm or so thickness is estimated to require at least about an order of magnitude more power to achieve comparable results. Moreover, even if a suitable high power source is available to use with a disk type device, there may still be a serious problem with heat generation. Much of the energy used by a sonophoresis transducer operating in an axial vibration and non-resonant mode is converted into heat and when the amount of power required is too high relative to the size of the device, it can become so hot as to burn the user.

Hence, the two conventionally known types of sonophoresis transducer devices suffer two major disadvantages: they are unduly large and heavy and/or they are quite inefficient (i.e., requiring a relatively large amount of power to achieve suitable permeation enhancement). There is accordingly an important need for a more efficient wave-generating transducer to enhance diffusion and permeation for use in transdermal/transmucosal sonophoresis, as well as other applications.

SUMMARY

It has now been found that diffusion of a substance in a liquid medium via sonophoresis, and particularly diffusion into and/or through a membrane, can be efficiently enhanced using a "flexure mode" transducer instead of a simple axial mode transducer as in conventional sonophoresis systems. The improved sonophoresis system of the present invention, using a flexure mode transducer, is much smaller and more efficient than conventional systems, which is particularly useful in the context of transdermal/transmucosal sonophoresis because it allows for small, lightweight devices with relatively low power requirements.

Flexure mode transducers—which are well known in certain other contexts unrelated to the present invention—produce in response to an electrical voltage signal a vibrating flexing action, rather than a simple expansion and contraction action. Flexure mode transducers can have various designs. A typical flexure mode transducer has at least one flexible layer of material, such as aluminum or titanium, joined to a piezoelectric layer, such as a piezoceramic. When the piezoelectric layer expands and contracts in response to a voltage signal, the joined flexible layer (which does not likewise expand and contract) forces the device to flex in order to accommodate the dimensional changes of the piezoelectric layer. Moreover, by applying a proper voltage signal frequency to the flexure mode transducer, a resonant flexure vibration response can be attained, thereby efficiently producing the desired acoustic waves. A flexure mode transducer can, for example, in its simplest form comprise at least one flexible disk layer bonded to at least one piezoelectric material disk layer. Multiple layers of one or both materials may also be used. A construction of one flexible layer joined to one piezoelectric layer is sometimes referred to as a "unimorph; and a construction of one piezoelectric layer sandwiched between two flexible layers is sometimes referred to as a "bimorph". The layers may be continuous or discontinuous. One variation is a ring design wherein the piezoelectric material forms a ring joined to the perimeter of a flexible disk layer. Radial or axial expansion and contraction of the piezoelectric ring in response to an alternating voltage signal causes the flexible layer inside the ring to flex axially in a vibrating drum-like fashion. Yet another variation is a piezoelectric material shaped to produce a flexure mode.

The preferred piezoelectric material comprises a piezoceramic, although other piezoelectric materials, such as piezopolymers may also be used. The flexible material preferably comprises a metal, such as aluminum, titanium, stainless steel, nickel, brass, and/or bronze. Also, the flexible layer may comprise another layer of piezoelectric material. The key characteristic of the flexible layer is simply that it does not expand and contract equally with the piezoelectric material layer, which thereby induces flexure. The selection of materials will depend on the particular intended application. The bottom surface of the transducer in contact with the liquid is preferably made of a material that does not react with the liquid and resists the erosive effect (pitting) that can be cause by cavitation. It may also be preferred to include relief structures (e.g., microreplicated structures) on the bottom, wave-generating surface of the transducer. Such structures may enhance the cavitation effect produced by the transducer by serving as nucleation sites for bubble formation, and may also be useful for directing the flow of liquid to desired locations on the transducer bottom, for example via channels, passages, and the like. However, such structures may also reduce the intensity of cavitation by trapping air pockets.

The flexible layer(s) may be joined to the piezoelectric material layer(s) in any number of ways: riveting, encasement, adhesive bonding, and the like. Further, it is preferred that the piezoelectric material be encased on its exposed outer surface by a coating of chemically inert, electrically insulating potting material, such as a polymer resin (e.g., epoxy). This potting layer is particularly desirable when the device is to be used for transdermal/ transmucosal sonophoresis.

A voltage signal source having a suitable frequency and power is applied to the piezoelectric material. The preferred frequency for transdermal/transmucosal sonophoresis is from about 10 kHz to about 20 MHz, more preferably from about 15 kHz to about 100 kHz. The voltage (rms) of the applied signal is generally from about 30V to 300V, although lower voltages are preferred where a suitably responsive piezoelectric material is used. Typically, electrical leads are mounted in electrical contact with the piezoelectric material, for example with one lead on the top side of the piezoelectric layer and the other lead on the bottom side, sandwiched between the piezoelectric material and the flexible material. The voltage signal source may be a separate unit connected to the transducer, or it may be integrated with the transducer apparatus, for example using a battery for the power supply and an integrated circuit chip to generate the desired voltage signal. One of the major advantages of the present invention is that the power requirements to achieve sonophoresis are very low compared with a conventionally constructed device of comparable size. Generally, depending on the application, the power required will be between about 0.05 and 5 $W/cm^2$, preferably from about 0.05 to about 1 $W/cm^2$, and most preferably (especially for transdermal/transmucosal sonophoresis) from about 0.05 to about 0.4 $W/cm^2$.

The voltage signal applied is typically sinusoidal, although other wave patterns may be used. It is also possible to enhance efficiency of the device by utilizing a duty cycle, i.e., period during which the signal is applied, of less than 100 percent. Reducing the duty cycle below 100 percent does not necessarily result in a commensurate reduction in sonophoresis effectiveness. In the context of transdermal/ transmucosal drug delivery and monitoring of body fluids, the duty cycle is preferably from about 5 to 95 percent, and more preferably from about 10 to 30 percent.

Depending on the particular application, the sonophoresis apparatus must generally be retained in a certain position, for example directly or indirectly (i.e., in compression wave communication) against the skin/mucosa. Since the transducer needs to flex in a vibrating action, it is preferred to hold the transducer at the nodal region of least flexure motion and avoid holding the transducer at those portions that undergo the most movement—i.e., the antinodes. For example, in the case of a bilayer disk shaped transducer vibrating in simple harmonic resonance, antinodes are located at the center and perimeter of the disk. There is a circular region, or nodal ring, between the antinodes where movement due to flexing is at a minimum. It is preferred to hold the transducer by contacting it with, for example, a suspending harness only along this circular nodal region. Also, it has been found that the wave energy, and thus sonophoresis effect, tends to be focused at the center portion of the device, which can be an important consideration in the design of the device for different purposes.

In the case of transdermal/transmucosal drug delivery, a drug containing layer is preferably disposed between the bottom of the transducer (or acoustic wave transmission means) and the dermal/mucosal tissue. The drug is preferably in a liquid medium as a solution or suspension. The drug-containing medium is preferably retained in a reservoir comprising a sponge-like or other absorbent matrix in order to maintain it in a position subject to the acoustic waves. The drug also may be retained in an adhesive layer that assists with adhesion of the device to the skin/mucosal surface. It may also be preferred in some cases to contain the drug medium in a reservoir formed, for example, in a housing holding the flexure mode transducer. The drug medium is then preferably conducted from the reservoir to the proper location between the skin/mucosa and transducer via passages, channels, and/or by absorbent matrix material, and the like. As noted above, the wave energy tends to be focused at the region below the center of the transducer, so it generally will be desirable to provide the drug medium to this focused area. It should also be noted that varying the geometry of the transducer can vary the effective focusing area.

The present invention is particularly useful for enhancing permeation of relatively large molecules into and/or through the skin/mucosa, molecules that do not sufficiently penetrate using conventional passive delivery systems (or do not do so quickly enough for the desired application). It can be used for delivering drugs into and/or through the dermal/mucosal tissue, as well as for noninvasively obtaining samples of bodily fluids for monitoring purposes and the like. For example, the present invention will be useful for obtaining biologic diagnostic samples, such as for glucose monitoring and the like.

As used herein, the term drug is intended to broadly include any active therapeutic or diagnostic substance, for example, antigens, haptens, antibodies, proteins, peptides, amino acids, carbohydrates, hormones, steroids, vitamins, lipids, nucleic acids, trace elements, conventional therapeutic drug compounds, bacterium, viruses, metabolites and body fluids.

It should also be emphasized that the present invention is useful both for transdermal/transmucosal systemic delivery (i.e., delivering drugs systemically through the dermal/mucosal tissue), as well as transdermal/transmucosal topical delivery (i.e., depositing drugs topically into the dermal/mucosal tissue). Transdermal topical drug delivery is important, for example, because many times topically applied antibiotics do not otherwise reach bacteria residing within the skin, such as in hair follicles. With the present invention it will be possible to selectively deliver drugs deep within and/or through the dermal/mucosal tissue.

Some preferred examples of drugs for use with the present invention include antianginals (e.g., verapamil, sotalol), antiarrhythmics (e.g. amiodarone, flecainide), antibacterials (e.g., cefprozil, nitrofurantoin, azithromycin, cefixime, clarithromycin, ciprofloxacin, cefuroxime, loracarbef, ofloxacin, cefpodoxime, amoxicillin, cefadroxil), anticonvulsants (e.g., clonazepam, phenytoin, lamotrigine, valproic acid, gabapentin, carbamazepine), antidepressants (e.g., nefazodone, fluvoxamine), antidiabetics (e.g., glipizide, glyburide, metformin), antidiuretics (e.g., desmopressin), antiemetics (e.g., ondansetron), antifungals (e.g., itraconazole), antihistamines (e.g., terfenadine), antihyperlipoproteinemics (e.g., lovastatin, pravastatin), antihypertensives (e.g., nifedipine, enalapril, quinapril, doxazosin, captopril, benazepril, diltiazem, losartan, fosinopril), antiinflammatories (e.g., diclofenac, ketoprofen, nabumetone, etodolac, oxaprozin, mesalamine, naproxen), antineoplastics (e.g., leuprolide, flutamide), antiparkinsonians (e.g., bromocriptine), antipsychotics (e.g., clozapine), antithrombotics (e.g., ticlopidine, enoxaparin), antiulcers (e.g., omeprazole, famotidine, lansoprazole, cimetidine, ranitidine, nizatidine), antivirals (e.g., saquinavir, acyclovir, famciclovir, lamivudine, stavudine, zidovudine), anxiolytics (e.g., alprazolam), cardiotonics (e.g., digoxin), central nervous system stimulants (e.g., pemoline), diuretics (e.g., isosorbide, triamterene), hormones (e.g., insulin, medroxyprogesterone), hypnotics (e.g., zolpidem), immunosuppressants (e.g., cyclosporin, azathioprine), narcotic analgesics (e.g., butorphanol, morphine), peristaltic stimulants (e.g., cisapride), treatments for benign prostatic hypertrophy (e.g., finasteride), and vasodilators (e.g., pentoxifylline), and pharmaceutically acceptable salts, solvates, esters, complexes, derivatives and stereoisomers thereof.

Particularly preferred drugs include leuprolide, insulin, famotidine, pravastatin sodium, enoxaparin and cisapride, and pharmaceutically acceptable salts, solvates, esters, complexes, derivatives and stereoisomers thereof.

It will be understood that other excipients may also be included, such as penetration enhancers, anti-irritants, and the like.

Accordingly, in one aspect the present invention provides a method of enhancing diffusion of a substance through a liquid by sonophoresis, comprising the steps of:

placing a flexure mode transducer in fluid communication with a liquid medium containing a substance to be diffused through the liquid; applying an alternating electrical voltage signal to the flexure mode transducer so as to cause the flexure mode transducer to vibrate and produce acoustic waves that enhance diffusion of the substance through the liquid.

Another aspect of the invention provides a method of enhancing the permeation of a substance through a membrane, comprising the steps of:

placing a flexure mode transducer in fluid communication with the membrane and the substance to be permeated through the membrane;

applying an alternating electrical voltage signal to the flexure mode transducer so as to generate acoustic wave vibrations at a frequency and intensity that enhance permeation of the substance at least partially through the membrane.

This method can be used for purposes such as transdermal/transmucosal drug delivery, body fluid monitoring as well as other purposes, such as for producing a filtered substance by enhancing the rate that a substance permeates through a filter membrane.

In a further aspect, the invention provides a flexure mode sonophoresis apparatus that enhances permeation of a substance across a membrane, comprising:

a flexure mode transducer in electrical communication with an alternating electrical voltage signal source that causes the flexure mode transducer to vibrate;

a membrane in fluid communication with the flexure mode transducer positioned so as to receive acoustic waves generated by the flexure mode transducer vibrations; and a substance in contact with the membrane that permeates at least partially through the membrane at an enhanced rate due to the acoustic waves generated by the flexure mode transducer.

In still another aspect of the invention there is provided a transdermal/transmucosal drug delivery device, comprising:

a flexure mode transducer adapted to be placed adjacent to a dermal or mucosal membrane, said flexure mode transducer responsive to an alternating electrical voltage signal source applied to the flexure mode transducer so as to cause the flexure mode transducer to vibrate and produce acoustic waves; and a therapeutically effective amount of a drug substance disposed in fluid communication with the flexure mode transducer such that vibration of the flexure mode transducer enhances permeation of the drug substance into the skin or mucosa.

BRIEF DESCRIPTION OF THE DRAWINGS

The present invention will be described with reference to the accompanying drawings where like reference numerals indicate corresponding or like components.

In the drawings.

DETAILED DESCRIPTION OF THE DRAWINGS

As used herein, the term "bottom" or "lower" surface refers to the surface that would be placed proximal to the skin/mucosa of a user (or other membrane, as the case may be), and "top" or "upper" surface refers to the surface that would be placed distal to the skin/mucosa of a user (or other membrane, as the case may be). The term "therapeutically effective" amount of a drug refers to an amount that is sufficient to achieve a desired physiological effect under the circumstances and conditions of the contemplated use. It is not practical in view of the wide variety of drugs and applications for the present invention to more specifically define what amount of a particular drug will be therapeutically effective. Nevertheless, those of ordinary skill in the art will be able to determine such amounts without difficulty or undue experimentation based upon their background knowledge and experience in conjunction with the disclosure of the present invention herein.

Figure 1:
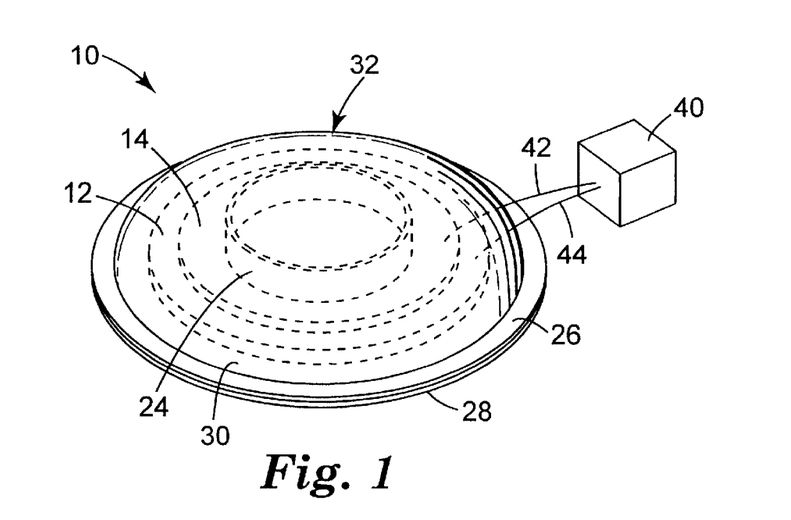
FIG. 1 is a perspective view of a transdermal/transmucosal sonophoresis device of the present invention.
Figure 2:
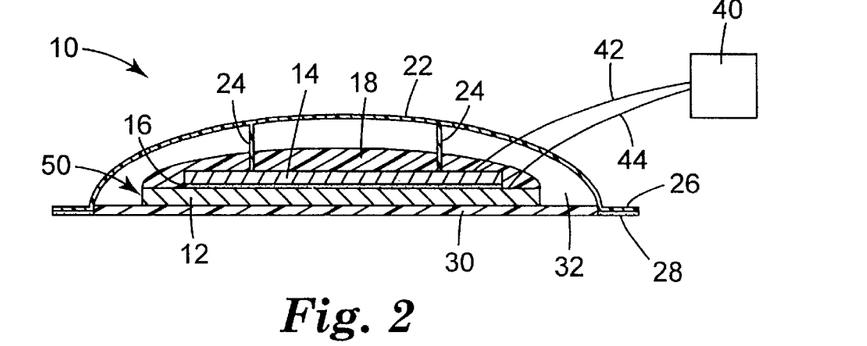
FIG. 2 is a cross sectional view of the embodiment of FIG. 1.

FIGS. 1 and 2 show a perspective and cross-sectional view, respectively, of device 10, which is a preferred embodiment of the invention designed for transdermal drug delivery. As best seen in FIG. 2, device 10 includes a flexible disk 12, preferably made of titanium, and a piezoelectric disk 14, preferably made of a piezoceramic material (e.g., PZT4 or PZT8, Manufactured by Morgan Matroc, Inc. or Keramos, Inc. or Aura Ceramics, Inc.). Other preferred materials for the flexible layer include aluminum and brass. One surface of the flexible disk is roughened as preparation for adhesion, preferably by sandblasting, rough sanding, or MEK (methyl ethyl ketone) etching. An adhesive bonding layer 16, preferably made of a high peel, high shear strength, high temperature and high electrical conductivity bonding adhesive joins the flexible layer 12 and the piezoelectric layer 14 together. Hysol EA9432NA manufactured by Dexter Corp. is a preferred bonding adhesive, as well as 3M™ brand DP460, DP100, 1751B/A (Minnesota Mining and Manufacturing Company, St. Paul, Minn., USA), and Hysol 9460. It may also in some cases be preferable for the bottom surface of the flexible layer to be plated with nickel or chromium in order to reduce the potential for corrosion The flexible disk 12 joined to the piezoelectric disk 14 collectively form a flexure mode transducer assembly 50 (best seen in FIG. 2, and as 150 in FIG. 3, discussed below).

Referring to FIGS. 1 and 2, a negative electrical lead 44 is conductively bonded to the negative electrode (bottom surface) of the piezoelectric layer 14. The lead may be soldered to copper tape held between the two disks, or the lead may be soldered directly to the flexible layer 12 (as shown), so long as there is sufficient electrical conduction from the flexible layer 12 to the bottom of the piezoelectric layer 14. More preferably the tip of the lead 44 is squeezed between the flexible layer 12 and the piezoelectric layer 14 (not shown). A positive electrical lead 42 is conductively bonded to the positive electrode (top surface) of the piezoelectric layer 14, preferably by soldering. It will be understood by those skilled in the art that any suitable configuration may be used so long as an electrical voltage signal can suitably be applied across the piezoelectric material.

As seen in FIG. 2, the upper surface of the transducer assembly 50 comprising flexible disk 12 and piezoelectric disk 14 is "potted" or coated in a layer of potting material 18. Potting layer 18 is preferably made of a polymer adhesive resin such as Plastidip™, 3M brand DP270 or DP100 or any coating or layer of electrically non conducting material, which serves as electrical and chemical insulation, as well as helping to anchor a cup-like suspending harness 24 and the electrical leads 42 and 44 in place. The cup-like suspending harness 24 (best seen in FIG. 1) is part of the housing cover 22 (best seen in FIG. 2). The housing cover 22 is made of any suitable plastic or other material. A peripheral flange 26 on housing cover 22 provides a surface to which a bioadhesive ring layer 28 may be adhered. The bioadhesive used, if any, will of course depend on the particular application for the device (e.g., the intended location and duration of adhesion).

In the particular embodiment shown, a drug-containing matrix layer 30, best seen in FIG. 2, is disposed at the bottom surface of the flexible disk 12. The matrix layer 30 may preferably be made of a sponge-like or other absorbent material that can retain a therapeutically effective amount of a drug-containing liquid in position beneath the transducer assembly. The matrix layer 30 may also partially or entirely comprise an adhesive in order to contain the drug and/or adhere the layer to the flexible layer, the skin/mucosa, or both. It will also be understood that many suitable alternatives exist for providing a drug or other substance in proper position. For example, a liquid, gel, or cream composition could be coated on the bottom surface of the transducer assembly or directly to the skin/mucosa prior to use. Another option is to use a separate drug-containing adhesive patch over which the flexure mode transducer can be placed. Such patch may be a drug-in-adhesive type patch, having the drug mixed directly into the adhesive, or a reservoir type patch, having the drug contained in a particular reservoir chamber portion of the patch. One possible advantage of using separate patches for providing the therapeutically effective amount of drug is that they can be easily replaced without having to replace the transducer apparatus.

A reservoir 32 formed between the housing cover 22 and the transducer assembly 50 may advantageously be used to contain, for example, a drug-containing liquid. If so, the liquid (not shown) may preferably be wicked into position under the bottom of the transducer by the matrix layer 30. Channels, passages, and the like (not shown) may be formed in the matrix layer 30 or the flexible disk 12 in order to help transport liquid from reservoir 32 into position beneath the transducer assembly 50.

It may also be desirable in certain applications to provide the bottom surface of transducer assembly 50, in this case flexible disk 12, with relief structures such as, for example, a microreplicated waffle-like or pin pattern. Such structures could be directly formed on the bottom of the flexible disk 12 or a microstructured polymer film may be applied. It is believed that such structures may enhance the cavitation effect produced by the transducer by serving as nucleation sites for bubble formation.

Figure 3:
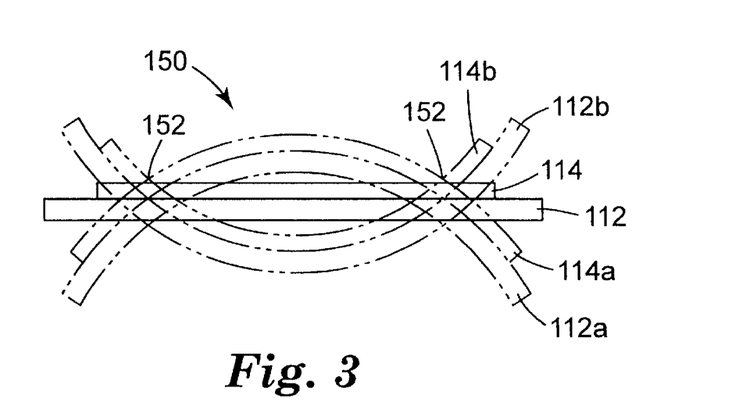
FIG. 3 is a cross sectional illustration showing the flexing action of a bilayer flexure mode transducer.

The transducer assembly 50 is actuated by applying an alternating electrical voltage signal source 40 (shown diagrammatically) to the piezoelectric disk 14 via the negative and positive leads 42, 44. This causes the transducer assembly to flex vibrationally, as shown in FIG. 3, which is a side view of a flexure mode transducer assembly 150, comprising a flexible layer 112 joined to a piezoelectric layer 114, showing an exaggerated flexing action. An applied voltage signal causes the piezoelectric layer 114 to expand, thus causing the transducer to flex, as shown with dashed lines as layers 114a and 112a. When the voltage signal reverses polarity, the piezoelectric layer contracts, thus causing the transducer to flex in the opposite direction, as shown with dashed lines as layers 114b and 112b. It can be seen that the greatest flexing movement occurs at the center and outer edge of the disk. These areas of greatest flexing action are called antinodes. Located between the antinodes is an region of least flexing movement, called a nodal ring 152. As best seen in FIGS. 1 and 2, the suspending harness 24 is preferably positioned to hold the transducer assembly 50 along the nodal ring of the disk. This positioning minimizes the damping effect that would otherwise occur by holding the transducer elsewhere.

The preferred signal frequency and voltage will of course depend substantially on the size, type and number of the piezoelectric material and flexible layers used, which in turn will depend on the intended application of the device. For a transdermal drug delivery or body fluid monitoring as in FIGS. 1 and 2, the thickness of the transducer assembly 50 (piezoelectric disk 14, bonding adhesive 16, and flexible 12) is preferably less than about 1 cm thick. The surface area of the bottom surface toward the skin is preferably from about 10 to 50 $cm^2$. The voltage signal is typically sinusoidal in form and preferably has a frequency of from about 10 kHz to about 20 MHz and more preferably from about 15 to 100 kHz. The particular frequency applied is preferably such as to cause the transducer assembly to vibrate at resonance. The rms voltage of the voltage signal typically ranges from about 30 to 300 V. Such a device may be expected to require on the order of about 0.05 to about 5 $W/cm^2$ of power to provide suitable permeation enhancement, and preferably from about 0.05 to about 1 $W/cm^2$, and more preferably from about 0.05 to about 0.4 $W/cm^2$.

The flexure mode transducer assembly 50 may be operated continuously or at a reduced duty cycle with intermittent bursts. For transdermal/transmucosal drug delivery and body fluid monitoring, the duty cycle is preferably from about 5 percent to about 95 percent, and more preferably from about 10 to about 30 percent. Such reduced duty cycle helps to conserve power while still providing sufficient permeation enhancement.

Experimental Testing

Figure 4:
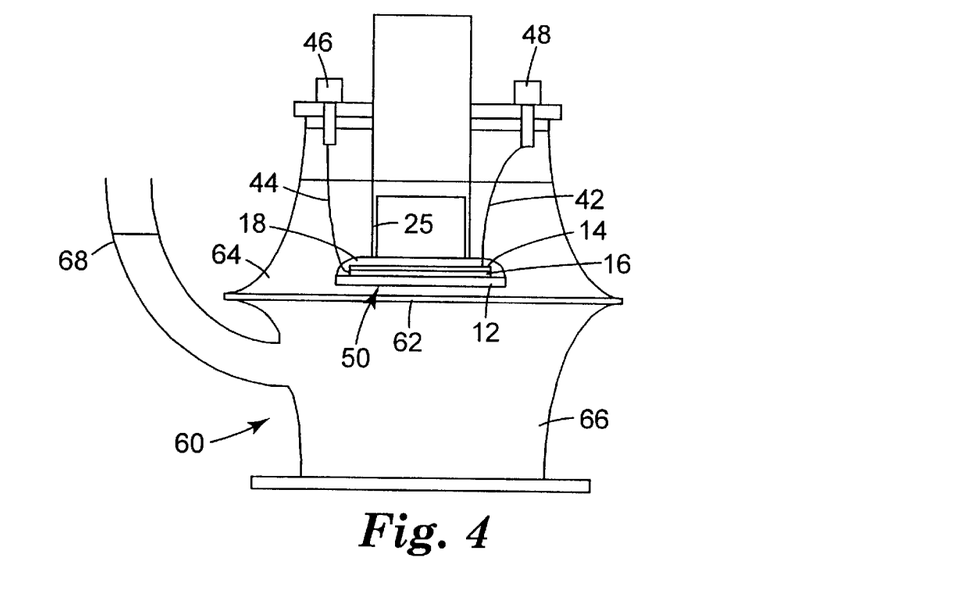
FIG. 4 is a diagrammatic side view of Franze cell testing apparatus used in testing the present invention.

Transmembranal sonophoresis testing using a flexure mode transducer was conducted using an apparatus commonly known as a Franz diffusion cell 60, shown in FIG. 4.

In examples 1 and 2, permeation tests were conducted using human cadaver skin. The Franz diffusion cell 60 was used to measure whether a drug substance contained in a donor liquid 64 permeated across a membrane, in this case cadaver skin 62, into the receptor liquid 66. About a 5 $cm^2$ flexure mode transducer 50, generally as described above, with a nickel plated flexible aluminum disk layer 12 bonded by adhesive 16 to piezoceramic disk layer 14 was used for the testing. The piezoceramic disk was from Morgan Matroc, Inc. (P/N 12050-4, PZT-4 disk). Both the aluminum and piezoceramic disks were about 0.127 cm thick. The aluminum disk had an outside diameter of about 2.54 cm and the piezoceramic disk had an outside diameter of about 1.9 cm. The bottom surface of the flexible layer 12 was essentially smooth, not patterned. An electrically insulating potting layer 18 was coated over the upper surface of the transducer.

The transducer assembly was suspended about 3 mm above the cadaver skin 62 by a cylindrical plastic suspending harness 25. An alternating electrical voltage signal source (not shown) was attached to a negative terminal 46 and positive terminal 48, which in turn were connected substantially as described above via electrical leads 44 and 42, respectively, to the piezoelectric disk 14. The transducer was actuated and samples from the lower liquid chamber were collected from sampling tube 68.

It should be noted that examples 1 and 2 are presented here for illustrative purposes only and that, although this type of in-vitro testing is in general considered very demonstrative, the testing in examples 1 and 2 was not optimized and may have contained flaws in some respects. These tests should be repeated and refined in order to establish conclusively the validity of the test results.

In example 3 below, a cavitation and permeation test was conducted using a Franz diffusion cell as described above, water color dye, and a synthetic membrane that is normally water impermeable. Example 3 clearly demonstrated the exceptional effectiveness of the flexure mode transducer at generating cavitation and enhancing permeation, which directly relates to the expected ability of the device to facilitate transdermal/transmucosal transport of substances.

EXAMPLE 1

Three Franz cells equipped with flexure mode sonophoresis transducers (active cells) were supplied with 70+ ml of phosphate buffer receptor fluid (ppb) and about a 7 $cm^2$ diffusion area of cadaver skin and a transducer of about the same size. For comparison, three different cells were used, not having any sonophoresis transducer (passive cells), and with 10 ml of receptor fluid (ppb) and 2 $cm^2$ cadaver skin diffusion area. About 20 ml of donor solution (ppb) with excess (beyond solubility levels) of morphine hydrochloride was added to the upper portion of each of the Franz cells atop the cadaver skin.

The power level applied initially to the sonophoresis transducers was about 1 $W/cm^2$, at a resonant frequency of about 26 kHz, at about 200 V (rms) with a continuous duty cycle. The experiment was conducted over a 5 hr time period. The three passive cells exhibited no detectable levels of morphine. The active cells exhibited about 100 micrograms/$cm^2$/hr for the first hour. Two active cells were then discontinued and showed a decrease down to 30 micrograms/$cm^2$/hr over the last four hour time period. The 7 $cm^2$ area showed on average a delivery rate of up to about twice the daily recommended rate of morphine delivery for humans.

Figure 5:
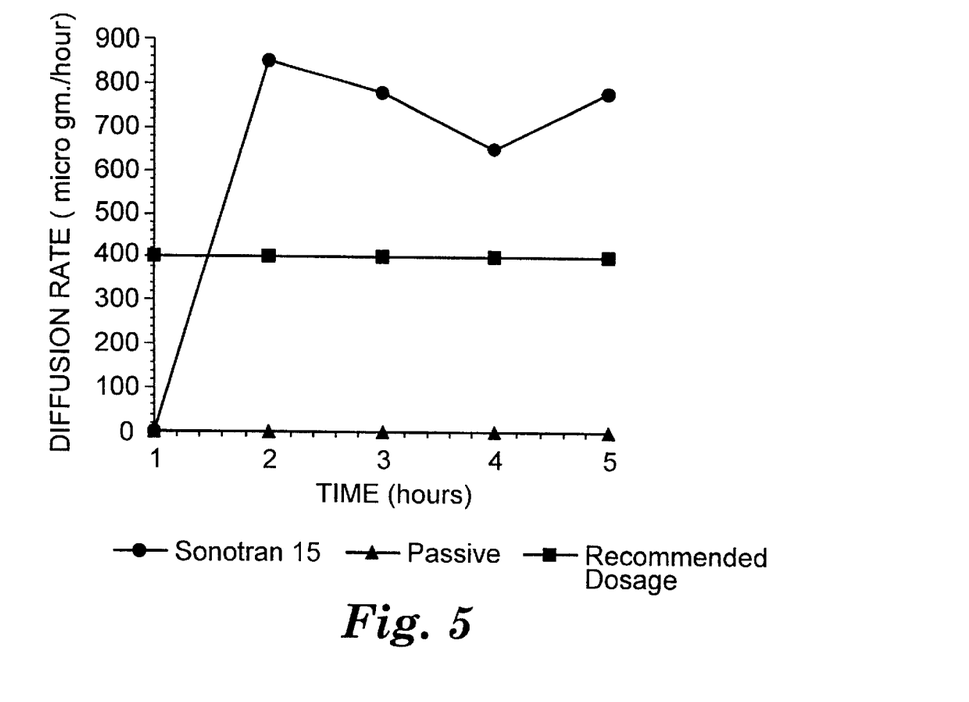
FIG. 5 is a graph of comparative test results using the present invention.

The results of this example are shown graphically in FIG. 5. Also, it is believed that heating produced in the transducers during the experiment due to the continuous operation at a 100% duty cycle shifted the resonant frequency from the operating frequency, significantly reducing the performance of the transducer.

EXAMPLE 2

A similar experiment to that described in Example 1 was carried out using salicylic acid. Again, three Franz cells equipped with flexure mode sonophoresis transducers were supplied with 70+ ml of receptor fluid (ppb) and about a 7 $cm^2$ diffusion area of cadaver skin with similar sized transducer. For comparison, four different passive cells were used, not having any sonophoresis transducer, and with 10 ml of receptor fluid (ppb) and 2 $cm^2$ cadaver skin diffusion area. About 20 ml donor solution (ppb) with excess (beyond solubility levels) of salicylic acid was added to the upper portion of the Franz cells atop the cadaver skin.

The power level applied initially to the sonophoresis transducers was about 2 $W/cm^2$, at a resonant frequency of about 27 kHz, about 200 V (rms) and with a continuous duty cycle. The experiment was conducted over a 5 hr time period.

Average passive drug flux was about 200 micrograms/cm$^2$/hr. Average sonophoretic drug flux during first few hours was about 700 micrograms/cm$^2$/hr.

Also, it is believed that heating produced in the transducers during the experiment due to the continuous operation at a 100% duty cycle shifted the resonant frequency from the operating frequency, significantly reducing the performance of the transducer. It is also believed that the substantial transport of salicylic acid in the passive case could be attributed to poor quality of the cadaver skin sample.

EXAMPLE 3

A qualitative experiment similar to that described in Example 1 was carried out using water with blue food coloring. A Franz cell was supplied with about 20 ml of blue donor solution, about 70+ ml of receptor fluid (water) and about a 7 cm$^2$ diffusion area of 3M brand Quant 1240-4c High Density Polyethylene porous film as the interposed membrane (which is impervious to water under normal conditions). The apparatus was equipped with a similarly sized (about 5 cm$^2$) flexure mode sonophoresis transducer.

The power level applied initially to the sonophoresis transducer was about 2 W/cm$^2$, at a resonant frequency of about 28.6 kHz, about 160 V (rms) and with a 20% duty cycle. The experiment was conducted over a 5 hr time period. It was observed that there was significant penetration of the blue liquid into the film. This demonstrates the ability of the transducer to enhance diffusion. Interestingly, the penetration appeared to occur only in an area of about 5 mm$^2$ immediately below the center of the transducer, which shows the ability of the device to focus the intensity of diffusion within the periphery of the nodal ring.

Although the foregoing invention has been described in terms of preferred embodiments, there is no intent to limit the scope of the invention to same. To the contrary, it is intended that the scope of the invention include all variations, many of which will be readily apparent to those skilled in the art reading the present disclosure, that utilize one or more of the general or specific aspects of the invention disclosed herein, as further set forth in the appended claims.

What is claimed is:

1. A method of enhancing diffusion of a substance through a liquid by sonophoresis, comprising the steps of:
    placing a flexure mode transducer in fluid communication with a liquid medium containing a substance to be diffused through the liquid;
    applying an alternating electrical voltage signal to the flexure mode transducer so as to cause the flexure mode transducer to vibrate and produce acoustic waves that enhance diffusion of the substance through the liquid.

2. The method of claim 1, wherein the flexure mode transducer comprises a piezoelectric material layer joined to a flexible layer such that the transducer flexes in response to application of the alternating electrical voltage signal to the piezoelectric material.

3. The method of claim 1, wherein the substance is a drug.

4. The method of claim 1, wherein the liquid is part of dermal or mucosal tissue.

5. The method of claim 1, wherein the flexure mode transducer is retained by a suspending harness that selectively holds the flexure mode transducer at a nodal region of the transducer.

6. The method of claim 1, wherein the transducer comprises a potting layer of electrically insulating material disposed over the transducer.

7. A method of enhancing the permeation of a substance through a membrane, comprising the steps of:
    placing a flexure mode transducer in fluid communication with the membrane and the substance to be permeated through the membrane;
    applying an alternating electrical voltage signal to the flexure mode transducer so as to generate acoustic wave vibrations at a frequency and intensity that enhance permeation of the substance at least partially through the membrane.

8. The method of claim 7, wherein the flexure mode transducer comprises a piezoelectric material layer joined to a flexible layer such that the transducer flexes in response to application of an alternating electrical voltage signal to the piezoelectric material.

9. The method of claim 8, wherein the piezoelectric material comprises a piezoceramic.

10. The method of claim 8, wherein the flexible layer comprises a metal.

11. The method of claim 10, wherein the metal is selected from the group consisting of titanium, aluminum, brass, nickel, stainless steel, and bronze.

12. The method of claim 8, wherein the piezoelectric material layer is joined to the flexible layer by an adhesive bonding layer.

13. The method of claim 8, wherein the piezoelectric material layer and flexible layer are each in the form of disks.

14. The method of claim 13, wherein the combined thickness of the disks is less than 10 mm.

15. The method of claim 7, wherein the membrane is a biological membrane.

16. The method of claim 15, wherein the biological membrane is dermal or mucosal.

17. The method of claim 15, wherein the substance to be permeated through the biological membrane is a drug.

18. The method of claim 17, wherein the drug is selected from the group consisting of verapamil, sotalol, amiodarone, flecainide, cefprozil, nitrofurantoin, azithromycin, cefixime, clarithromycin, ciprofloxacin, cefuroxime, loracarbef, ofloxacin, cefpodoxime, amoxicillin, cefadroxil, clonazepam, phenytoin, lamotrigine, valproic acid, gabapentin, carbamazepine, nefazodone, fluvoxamine, glipizide, glyburide, metformin, desmopressin, ondansetron, itraconazole, terfenadine, lovastatin, pravastatin, nifedipine, enalapril, quinapril, doxazositn, captopril, benazepril, diltiazem, losartan, fosinopril, diclofenac, ketoprofen, nabumetone, etodolac, oxaprozin, mesalamine, naproxen, leuprolide, flutamide, bromocriptine, clozapine, ticlopidine, enoxaparin, omeprazole, famotidine, lansoprazole, cimetidine, ranitidine, nizatidine, saquinavir, acyclovir, famciclovir, lamivudine, stavudine, zidovudine, alprazolam, digoxin, pemoline, isosorbide, triamterene, insulin, medroxyprogesterone, zolpidem, cyclosporin, azathioprine, butorphanol, morphine, cisapride, finasteride, and pentoxifylline, and pharmaceutically acceptable salts, solvates, esters, complexes, derivatives and stereoisomers thereof.

19. The method of claim 18, wherein the drug is selected from the group consisting of leuprolide, insulin, famotidine, provastin sodium, enoxaparin, cisapride, and pharmaceutically acceptable salts, solvates, esters, complexes, derivatives and stereoisomers thereof.

20. The method of claim 15, wherein the substance to be permeated through the biological membrane is contained in a bodily fluid.

21. The method of claim 7, wherein the alternating electrical voltage signal is in the form of a sinusoidal wave.

22. The method claim 7, wherein the alternating electrical voltage signal is applied in a duty cycle of between 10 and 30 percent.

23. The method claim 7, wherein the alternating electrical voltage signal supplies from 0.05 to 0.5 watts/cm$^2$ of power to the transducer.

24. The method of claim 7, wherein the alternating electrical voltage signal has a frequency so as to cause the transducer vibrate at resonance.

25. The method of claim 7, wherein the vibrating frequency is from 10 kHz to 20 MHz.

26. The method of claim 8, wherein the piezoelectric material layer is encased in a polymer resin potting material.

27. The method of claim 7, wherein the flexure mode transducer is retained in place adjacent to the membrane by a suspending harness that selectively holds the flexure mode transducer along a nodal region.

28. The method of claim 27, wherein the suspending harness comprises a plastic cover that forms a chamber between the cover and the flexure mode transducer.

29. The method of claim 28, wherein the cover is adhered to the membrane by a ring of adhesive.

30. The method of claim 28, wherein the chamber contains a supply of the substance to be permeated through the membrane.

31. The method of claim 7, wherein the substance to be permeated through the membrane is disposed between a bottom surface of the flexure mode transducer and the membrane.

32. The method of claim 30, wherein the substance to be permeated through the membrane is contained in a matrix.

33. The method of claim 32, wherein the matrix is a sponge-like material.

34. The method of claim 31, wherein the bottom surface of the flexure mode transducer has cavitation enhancing microstructures.

35. A process for producing a filtered substance by causing the substance to permeate through a membrane using the method of claim 7.

36. A flexure mode sonophoresis apparatus that enhances permeation of a substance across a membrane, comprising:

a flexure mode transducer in electrical communication with an alternating electrical voltage signal source that causes the flexure mode transducer to vibrate;

a membrane in fluid communication with the flexure mode transducer so as to receive acoustic compression waves generated by the flexure mode transducer vibrations; and a substance in contact with the membrane that permeates at least partially through the membrane at an enhanced rate due to the acoustic waves generated by the flexure mode transducer.

37. The apparatus of claim 36, wherein the flexure mode transducer comprises a layer of piezoelectric material joined to a flexible layer such that the transducer flexes in response to an alternating electrical voltage signal applied to the piezoelectric material.

38. The apparatus of claim 37, wherein the flexible layer comprises metal selected from the group consisting of titanium, aluminum, brass, nickel, stainless steel, and bronze.

39. The apparatus of claim 37, wherein the combined thickness of the piezoelectric material layer and the flexible layer is less than 10 mm.

40. The apparatus of claim 36, wherein the membrane is dermal or mucosal.

41. The apparatus of claim 40, wherein the substance to be permeated through the membrane is a drug.

42. The apparatus of claim 36, wherein the alternating electrical voltage signal source supplies from 0.05 to 1 watt/cm$^2$ of power to the transducer.

43. The apparatus of claim 36, wherein the vibrating frequency is from 10 kHz to 20 MHz.

44. A transdermal/transmucosal drug delivery device, comprising:

a flexure mode transducer adapted to be placed adjacent to a dermal or mucosal membrane, said flexure mode transducer being responsive to an alternating electrical voltage signal source applied to the flexure mode transducer so as to cause the flexure mode transducer to vibrate and produce acoustic waves; and a therapeutically effective amount of a drug substance disposed in fluid communication with the flexure mode transducer such that vibration of the flexure mode transducer enhances permeation of the drug substance into the skin or mucosa.

* * * * *

UNITED STATES PATENT AND TRADEMARK OFFICE
CERTIFICATE OF CORRECTION

PATENT NO. : 6,322,532 B1
DATED : November 27, 2001
INVENTOR(S) : Joseph M D'Sa and Jamieson C. Keister It is certified that error appears in the above-identified patent and that said Letters Patent is hereby corrected as shown below:

<u>Title page,</u>
Item [75], Inventors, please delete "Jaimeson" and insert in place thereof
-- Jamieson --

<u>Column 12,</u>
Line 47, please delete the word "doxazsitn" and insert in place thereof -- doxazosin --.

<u>Column 13,</u>
Line 3, after the word "method" and before the word "claim", please insert -- of --.
Line 6, after the word "method" and before the word "claim", please insert -- of --.

Signed and Sealed this

Eighth Day of October, 2002

Attest:

Attesting Officer

JAMES E. ROGAN
*Director of the United States Patent and Trademark Office*